(12) United States Patent
Saxena et al.

(10) Patent No.: US 8,008,328 B2
(45) Date of Patent: Aug. 30, 2011

(54) METHODS FOR THE TREATMENT OF DIABETES-ASSOCIATED DYSLIPDEMIA

(75) Inventors: Uday Saxena, Atlanta, GA (US); Sivaram Pillarisetti, Norcross, GA (US); Ish Khanna, Alpharetta, GA (US)

(73) Assignee: Reddy US Therapeutics, Inc., Norcross, GA (US)

( * ) Notice: Subject to any disclaimer, the term of this patent is extended or adjusted under 35 U.S.C. 154(b) by 239 days.

(21) Appl. No.: 12/005,887

(22) Filed: Dec. 28, 2007

(65) Prior Publication Data
US 2008/0214531 A1  Sep. 4, 2008

Related U.S. Application Data

(60) Provisional application No. 60/886,113, filed on Jan. 23, 2007, provisional application No. 60/986,002, filed on Nov. 7, 2007.

(51) Int. Cl.
| | | |
|---|---|---|
| *A61K 31/44* | (2006.01) | |
| *A61K 31/70* | (2006.01) | |
| *A61K 31/54* | (2006.01) | |
| *A61K 31/505* | (2006.01) | |
| *A61K 31/445* | (2006.01) | |
| *A61K 31/40* | (2006.01) | |
| *A61K 31/195* | (2006.01) | |
| *A61K 31/155* | (2006.01) | |

(52) U.S. Cl. ....... 514/356; 514/35; 514/226.5; 514/275; 514/315; 514/422; 514/563; 514/635; 514/866

(58) Field of Classification Search ............... 514/226.5, 514/356, 866, 35, 275, 315, 422, 563, 635
See application file for complete search history.

(56) References Cited

U.S. PATENT DOCUMENTS

| | | | | |
|---|---|---|---|---|
| 4,233,299 A | * | 11/1980 | Trummlitz et al. | ........ 514/226.5 |
| 6,469,035 B1 | * | 10/2002 | Cefali | ........................... 514/356 |
| 2006/0069161 A1 | | 3/2006 | Lee et al. | |

FOREIGN PATENT DOCUMENTS

| | | |
|---|---|---|
| WO | 2005002542 A2 | 1/2005 |
| WO | WO 2007041499 A2 * | 4/2007 |

OTHER PUBLICATIONS

Patent Cooperation Treaty, PCT International Search Report, mailing date Mar. 27, 2008, completion date Feb. 22, 2008, International Application No. PCT/US07/26456.
Tenenbaum, A. et al., "Atherogenic Dyslipidemia in Metabolic Syndrome and Type 2 Diabetes: Therapeutic Options beyond Statins" (2006) Cardiovascular Diabetology, vol. 5: No. 20; Sep. 26, 2006.
Chen, K. et al., "Antagonism of the Prostaglandin D2 Receptor 1 Suppresses Nicontinic Acid-Induced Vasodilation in Mice and Humans" PNAS. Apr. 25, 2006, vol. 103, No. 17, pp. 6682-6687.
WO 2004/010992 A1 (Desai et al.) Feb. 5, 2004.
American Heart Association, Circulation, Journal of the American Heart Association, NCEP Report, "Implications of Recent Clinical Trials for the National Cholesterol Education Program Adult Treatment Panel III Guidelines", Scott M. Grundy, et al., Circulation. 2004:110:227-239  DOI:  10.1161/01.CIR:0000133317.49796.OE and Correction p. 763. Downloaded from circ.ahajournals.org by on Feb. 26, 2009.
A. M. Pereira Arias, et al., "Indomethacin Does Not Affect Endogenous Glucose Production in Type 2 Diabetes Mellitus", Horm. Metab. Res. 2001:33:659-663.
Alberto M. Pereira Arias, et al., "Indomethacin Decreases Insulin Secretion in Patients With Type 2 Diabetes Mellitus", Metabolism, vol. 49, No. 7 (Jul. 2000), : pp. 839-849.
Evelien Dekker, et al., "Indomethacin Stimulates Glucose Production in Adults With Uncomplicated *Falciparum malaria*", Metabolism, vol. 47, No. 2 (Feb. 1998), : pp. 217-222.
Hyo-Kyung Han, et al., Research paper: "Improved absorption of meloxicam via salt formation with ethanolamines", ScienceDiet, European Journal of Pharmaceutics and Biopharmaceutics 65 (2007) pp. 99-103.
Remington's Pharmaceutical Sciences, 17th edition, Mack Publishing Company, Easton, PA, 1985, p. 1418.
Gennaro, A. R., Remington: The Science and Practice of Pharmacy, 20th Edition, (Lippincott, Williams and Wilkins), 2000.
Hoover, John E., Remington's Pharmaceutical Sciences, Mack Publishing Co., Eaton, Pennsylvania, 1975.
Liberman, et al., Eds., Pharmaceutical Dosage Forms, Marcel Decker, New York, NY, 1980.
Kibbe, et al., Eds., Handbook of Pharmaceutical Excipients (3rd Ed.), American Pharmaceutical Association, Washington, 1999.
Goodman & Gilman's The Pharmacological Basis of Therapeutics, Ninth Edition (1996), Appendix II, pp. 1707-1711.
PCT International Preliminary Report on Patentability, date of issuance Jul. 28, 2009, mailed Aug. 6, 2009, The International Bureau of WIPO, International Application No. PCT/US2007/026456, International Filing Date Dec. 28, 2007, Applicant Reddy US Therapeutics, Inc., et al.
European Communication pursuant to Rules 161 and 162 EPC, dated Sep. 9, 2009, European Patent Office, 2280 HV Rijswijk Netherlands, European Patent Application No. 07863294.0—1216 PCT/US2007026456, Applicant Reddy US Therapeutics, Inc.
Reply to the communication under Rule 161 and 162 EPC with new claims 1 to 15 to replace the claims previously on file, filed Sep. 24, 2009, in response to outstanding European Communication pursuant to Rules 161 and 162 EPC, dated Sep. 9, 2009, European Patent Office, 2280 HV Rijswijk Netherlands, European Patent Application No. 07863294.0—1216 PCT/US2007026456, Applicant Reddy US Therapeutics, Inc.
Communication Pursuant to Article 94(3) EPC, European Patent Office, dated Jul. 27, 2010, European Patent Application No. 07863294.0—2123 / 2120959, Applicant Dr. Reddy's Laboratories Ltd.

(Continued)

*Primary Examiner* — Kevin E Weddington
(74) *Attorney, Agent, or Firm* — Balaram Gupta; Robert A. Franks; Thomas C. McKenzie

(57) ABSTRACT

Methods for the treatment of insulin resistance, diabetes, and/or diabetes associated dyslipidemia by administering niacin and meloxicam are disclosed.

11 Claims, 5 Drawing Sheets

OTHER PUBLICATIONS

Communication with extended European search report, European Patent Office, dated Apr. 22, 2010, completed Mar. 19, 2010,European Patent Application No. 07863294.0—2123 / 2120959 PCT/US2007026456, Applicant Dr. Reddy's Laboratories Ltd.

Gonzalez-Ortiz M et al: "Inhibition of cyclooxygenase-1 or 2 on insulin sensitivity in healthy subjects" Horomone and Metabolic Research, vol. 33, No. 4, Apr. 2001, pp. 250-253, XP009131156.

Helmersson Johanna et al: "Association of type 2 diabetes with cyclooxygenase-mediated inflammation and oxidative stress in an elderly population" Circulation, Lippincot Williams and Wilkins, Baltimore, US, vol. 109, No. 14, Apr. 13, 2004, pp. 1729-1734, XP002488915.

Schmidt Maria Ines et al: "Diabesity: An inflammatory metabolic condition." Clinical Chemistry and Laboratory Medicine, vol. 41, No. 9, Sep. 2003, pp. 1120-1130, XP009131179.

Jungnickel P W et al: "Effect of two aspirin pretreatment regimens on niacin-induced catuneous reactions" Journal of General Internal Medicine, Philadelphia, PA, US, vol. 12, No. 10, Jan. 1, 1997, pp. 591-596, XP002956938.

* cited by examiner

METHODS FOR THE TREATMENT OF DIABETES-ASSOCIATED DYSLIPDEMIA

CROSS-REFERENCE TO RELATED PATENT APPLICATIONS

This application claims priority to U.S. Provisional Patent Application Ser. No. 60/886,113, filed Jan. 23, 2007, and U.S. Provisional Patent Application Ser. No. 60/986,002, filed Nov. 7, 2007, of which each are incorporated by reference herein in their entirety.

BACKGROUND OF THE INVENTION

The present invention relates to methods and compositions for the treatment of insulin resistance, diabetes, and/or diabetes associated dyslipidemia.

Diabetes is the fifth leading killer of Americans, with 73,000 deaths per year. Diabetes is a disease in which the body's failure to regulate glucose, or blood sugar, can lead to serious and even fatal complications. There are two types of diabetes, type 1 and type 2.

Type 2 diabetes is a metabolic disorder that is primarily characterized by insulin resistance, relative insulin deficiency, and hyperglycemia. Insulin resistance is defined as a decreased response of peripheral tissues to insulin action. Increasingly, insulin resistance has been recognized as the integral feature of metabolic syndrome, which includes glucose intolerance, insulin resistance, obesity, dyslipidemia, hypertriglyceridemia, low high density lipoprotein (HDL) cholesterol, hypertension, and accelerated atherosclerosis. Hyperinsulinemia and delayed clearance of glucose in an oral glucose tolerance test (OGTT) are hallmarks of insulin resistance in patients.

Typically, subjects suffering from type 2 diabetes are also likely to have dyslipidemia (i.e., diabetic dyslipidemia), where the subjects have abnormally low levels of HDL and/or abnormally high levels of low density lipoprotein (LDL), cholesterol, and/or abnormally high levels of triglycerides. Type 2 diabetic subjects may have a preponderance of smaller, denser LDL particles, which can also possibly increase atherogenicity even if the absolute concentration of LDL cholesterol is not abnormally high. The low levels of HDL (i.e. <40 mg/dL) and/or high levels of LDL (i.e. >100 mg/dL) and/or high levels of triglycerides (i.e. >150 mg/dL) increase the risk of atherosclerosis and the risk for developing cardiovascular disease in the diabetic population. For further information, see the National Cholesterol Education Program (NCEP) update on the Adult Treatment Panel (ATP) III guidelines, *Circulation*; 110:227-239 (2004).

Niacin (Vitamin $B_3$) is a water-soluble vitamin whose derivatives play essential roles in energy metabolism in the living cell and in DNA repair. Other functions of niacin include removing toxic chemicals from the body and assisting in the production of steroid hormones. Niacin, when taken in large doses, blocks the breakdown of fats in adipose tissue, thus altering blood lipid levels. Niacin is used in the treatment of dyslipidemia because it reduces very low density lipoprotein (VLDL), a precursor of LDL cholesterol. Because niacin blocks the breakdown of fats, it causes a decrease in free fatty acids in the blood and consequently, decreased secretion of VLDL and cholesterol by the liver.

By lowering VLDL levels, niacin also increases the level of HDL or "good" cholesterol in blood, and therefore, it is sometimes prescribed for patients with low HDL, who are also at high risk of a heart attack.

High dose niacin has been shown to elevate fasting blood sugar levels, thereby worsening type 2 diabetes. Accordingly, niacin is contra-indicated for persons with type 2 diabetes. The mechanism behind niacin-induced insulin resistance and diabetes is presently unknown. It is believed, however, that insulin actions are mediated by insulin receptors present in tissues that utilize glucose and it is conceivable that impaired receptor signaling in the presence of niacin may contribute to niacin-induced insulin resistance.

Patients taking pharmacological doses of niacin (ranging from 0.5-3 g per day) often experience an array of side effects that can include one or more of dermatological complaints (facial flushing and itching, dry skin, and skin rashes including acanthosis nigricans). Facial flushing is the most commonly reported side effect of niacin and is so severe that many patients discontinue niacin treatment as a result. The flushing has been shown to be caused by the result of cutaneous vasodilation resulting from niacin induced release of prostaglandins (e.g., prostaglandin D2, (PGD2)) in the skin.

Nonsteroidal anti-inflammatory drugs (NSAIDs) comprise a heterogeneous group of medications with analgesic, antipyretic, and anti-inflammatory actions. These drugs are widely used to control fever and acute or chronic pain. They are the most sold medications worldwide and, together with analgesics and antipyretics, account for approximately 30% of all medicines used.

NSAIDs are typically contra-indicated for diabetes sufferers, demonstrating some incidence of gastrointestinal bleeds in patients taking NSAIDS. Some NSAIDs have been shown to exacerbate insulin resistance. See e.g., Pereira Arias, A., et. al., *Horm. Meta. Res.* 2001:33(11); 659-63; and Pereira Arias, A., et al., *Metabolism.* 2000:49(7): 839-44; and Dekker, E., et. al., *Metabolism,* 1998; 47(2): 217-22.

Meloxicam is a NSAID that is used to relieve the symptoms of arthritis, primary dysmenorrheal, fever, and as an analgesic, especially where there is an inflammatory component. Meloxicam has been shown to significantly decrease symptoms of pain and stiffness in patients, with a low incidence of gastrointestinal side effects. In models, it exhibits anti-inflammatory, analgesic, and antipyretic activities. Its mechanism of action may be related to Cox inhibition. Meloxicam has been shown, to inhibit Cox-2 preferentially over Cox-1 to some degree.

SUMMARY OF THE INVENTION

Briefly, therefore, the invention is directed to a method of treating dyslipidemia in a subject having type 2 diabetes. The method includes administering to the subject niacin in combination with meloxicam.

In another aspect, the invention is a method of reducing the level of prostaglandins in a diabetic subject to whom niacin has been administered. The method includes administering meloxicam to the subject in an amount sufficient to reduce the prostaglandin levels in the subject.

In a different aspect, the invention is a method of reducing niacin-induced flushing in a diabetic subject to whom niacin has been administered. The method includes administering meloxicam to the subject in an amount sufficient to reduce the flushing in the subject.

In another aspect, the invention is a method of treating hyperinsulinemia and dyslipidemia in a diabetic subject in need of such treatment. The method includes administering meloxicam and niacin to the subject in therapeutically effective amounts.

In yet another aspect, the invention is a method of treating type 2 diabetes and related dyslipidemia in a subject. The method includes administering niacin to the subject in combination with meloxicam in therapeutically effective amounts, whereby the meloxicam reduces insulin resistance and reduces niacin-induced flushing in the subject.

In a different aspect, the invention is method of treating low HDL in a subject having type 2 diabetes. The method includes administering meloxicam and niacin to the subject.

In still another aspect, the invention is a method of treating low HDL and high LDL in a subject having type 2 diabetes and related dyslipidemia. The method includes administering meloxicam, niacin, and at least one statin to the subject.

In another aspect, the invention is a method of treating niacin-induced insulin resistance and niacin-induced flushing in a subject having type 2 diabetes and related dyslipidemia. The method includes administering meloxicam and niacin to the subject.

In another aspect, the invention is a method of identifying compounds that reduce niacin-induced flushing and reduce niacin-induced insulin resistance in a combination with niacin in a manner that is substantially similar to meloxicam. The method includes measuring the effectiveness of the test compound in reducing niacin induced flushing; measuring the effectiveness of the test compound in reducing niacin induced insulin resistance; comparing the effectiveness of the test compound in reducing niacin induced flushing and in reducing niacin induced insulin resistance to the effectiveness of meloxicam in the same tests under the same conditions; and selecting compounds that reduce niacin-induced flushing and reduce niacin-induced insulin resistance to a degree that is substantially similar or superior to meloxicam.

These and other aspects of the invention will be understood and become apparent upon review of the specification by those having ordinary skill in the art.

DETAILED DESCRIPTION OF ILLUSTRATIVE EMBODIMENTS

Figure 1:
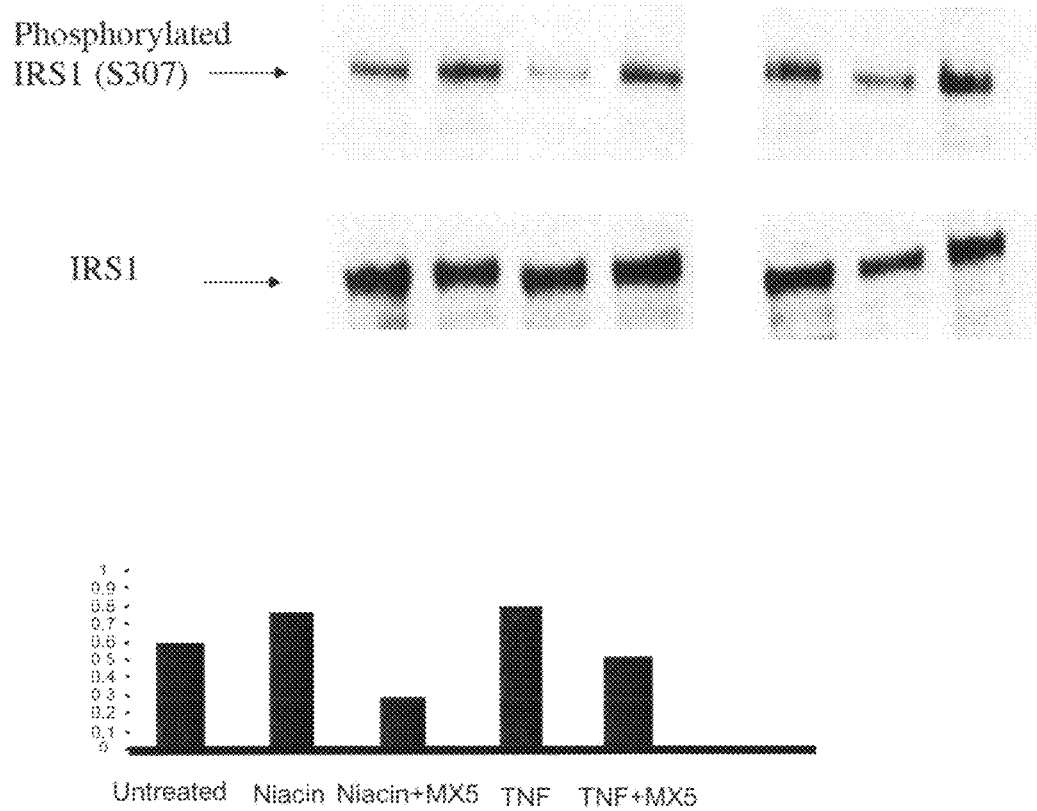
FIG. 1 is a chart demonstrating the effect of meloxicam on niacin-induced phosphorylation of insulin receptor substrate (IRS-1)

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features and aspects of the present invention are disclosed in or are apparent from the following detailed description. It is to be understood by one of ordinary skill in the art that the present discussion is a description of exemplary embodiments only, and is not intended as limiting the broader aspects of the present invention.

Based on the research studies, it has been unexpectedly discovered that meloxicam may be used for the treatment and/or prevention of insulin resistance in type 2 diabetics. Those having ordinary skill in the art would recognize that NSAIDs are typically contra-indicated for treatment in diabetics, with studies demonstrating that diabetics are at higher risk for heart failure, renal failure, and gastrointestinal problems when taking NSAIDs. The inventors unexpectedly discovered that administration of meloxicam to diabetics results in a partial or full decrease in niacin-induced insulin resistance, thereby providing a therapeutic benefit to diabetic subjects suffering from the associated insulin resistance. Moreover, the administration of meloxicam also assists in the treatment and/or prevention of diabetic dyslipidemia and the prevention of the side effect of niacin-induced flushing when administered in combination with niacin.

As used herein, the term "dyslipidemia" refers to abnormally high levels of LDL and/or abnormally low levels of HDL. As used herein, an abnormally high level of LDL is any level of LDL over 100 mg/dL and an abnormally low level of HDL is any level that is lower than 40 mg/dL. Stated differently, the present invention encompasses the treatment of dyslipidemia conditions such as hyperlipidemia, hypolipidemia, elevated triglycerides, hypercholesterolemia, hyperglyceridemia, and hypertriglyceridemia. The present invention also encompasses the treatment of diabetic atherosclerosis.

Previously, those having ordinary skill in the art recognized that administration of niacin to diabetic subjects suffering from insulin resistance may exacerbate the insulin resistance condition. Niacin is typically contra-indicated for diabetics due to the side effect of increasing insulin resistance and, thus, elevation of fasting blood sugar levels. Accordingly, it has been recognized that higher dosages of niacin often increase the insulin resistance in diabetic subjects. The inventors unexpectedly discovered that when niacin is administered in combination with meloxicam, diabetics demonstrate a partial or full reduction in the aforementioned niacin-induced insulin resistance.

In addition, the research studies by the inventors unexpectedly led to the discovery that the administration of meloxicam reduces the production of prostaglandins released when a subject is administered niacin to treat dyslipidemia, such that the subject does not suffer from the unwanted side effect of flushing.

In the present invention, it has been found that, when administered with meloxicam, niacin is a suitable treatment and/or prevention of diabetic dyslipidemia. It is preferred that the methods and compositions of the present invention are used in the treatment and/or prevention of diabetes and/or related dyslipidemia in a subject, and in preferred embodiments, the subject is one that is in need of treatment or prevention of diabetes and/or related dyslipidemia.

The terms "treating" or "to treat" mean alleviation of symptoms, elimination of the causation, either on a temporary or permanent basis, or the prevention of slowing of the appearance of symptoms. The term "treatment" means alleviation, elimination of causation of, or prevention of any of the diseases or disorders described herein.

In one aspect, therefore, the invention is a combination therapy for the treatment and/or prevention of type 2 diabetes insulin resistance and/or associated dyslipidemia. Thus, the present invention encompasses the administration of meloxicam in combination with niacin to a subject.

As used herein, the term "subject" includes any human or animal subject, and, preferably, a subject that is in need of the prevention or treatment of type 2 diabetes and/or related dyslipidemia. For purposes of prevention, the term refers to any subject, and, preferably, is a subject that is at risk for, or is predisposed to, developing diabetes and/or related dyslipidemia. For purposes of treatment, the term refers to any human or animal subject, and in some embodiments, is a subject that is suffering from any symptom of diabetes and/or related dyslipidemia. As used herein, the term "subject is in need of the treatment or prevention of diabetes and/or related dyslipidemia" refers to any subject who is suffering from or is predisposed to any diabetes and/or related dyslipidemia described herein.

For ease of reference, the present invention will be described with reference to administration to human subjects. It will be understood, however, that such descriptions are not limited to administration to humans, but will also include administration to other animals, such as mammals, unless explicitly stated otherwise. For example, besides being useful for human treatment, these combinations are also useful for treatment of mammals, including horses, dogs, cats, rats, mice, sheep, pigs, etc.

A first component of the present invention is meloxicam and/or its pharmaceutically acceptable salts. Meloxicam belongs to the class of NSAID drugs called the enolic acid group and has the structure:

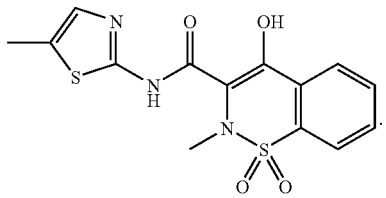

Meloxicam has the IUPAC name: 8E)-8-[hydroxy-[(5-methyl-1,3-thiazol-2-yl)amino]methylidene]-9-methyl-10,10-dioxo-10λ6-thia-9-azabicyclo[4.4.0]deca-1,3,5-trien-7-one. It has the CAS number 71125-38-7, ATC code M01AC06, a molecular formula of $C_{14}H_{13}N_3O_4S_2$ and a molecular mass of 351.403 g/mol.

As used herein, the term "meloxicam" encompasses meloxicam or a compound other than meloxicam itself which the body metabolizes into meloxicam, thus producing the same effect as described herein.

Meloxicam, including methods of synthesis, is described in EP 0 002 482 and U.S. Pat. No. 4,233,299. Meloxicam that is useful in the present invention may be synthesized or may be obtained commercially. Any grade or purity of meloxicam may be used that is appropriate for use in human pharmaceutical preparations.

A second component of the present invention is niacin and/or its pharmaceutically acceptable salts. Niacin has the IUPAC name: nicotinic acid, or pyridine-3-carboxylic acid. It has the CAS number 59-67-6, the molecular formula $C_6H_5NO_2$, and a molar mass of 122.102.

In certain aspects of the present invention, niacin (used interchangeably herein as "vitamin $B_3$" or nicotinic acid is available over-the counter from many commercial sources. Niacin has the general structure:

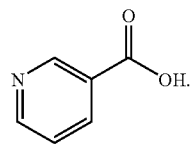

As used herein, the term "niacin" encompasses niacin or a compound other than niacin itself which the body metabolizes into niacin, thus producing the same effect as described herein. For example, the liver can synthesize niacin from the essential amino acid tryptophan. The other compounds specifically include, but are not limited to, nicotinyl alcohol tartrate, d-glucitol hexanicotinate, aluminum nicotinate, niceritrol, and d,1-alpha-tocopheryl nicotinate. Each such compound will be collectively referred to hereinbelow by "niacin."

In conventional therapies, niacin is typically administered one to four times per day after meals, depending on the dosage form selected. Typical doses range from about 0.5 grams to about 3 grams daily.

Niacin is currently available in different dosage forms. One dosage form is an immediate or rapid release tablet which is designed to be administered three to four times per day. Immediate release (IR) niacin formulations generally release nearly all of their niacin within about 30 to 60 minutes following administration.

The components that are useful in the present invention can be of any purity or grade, as long as the preparation is of a quality suitable for pharmaceutical use. The components can be provided in pure form, or they can be accompanied with impurities or commonly associated compounds that do not affect their physiological activity or safety.

Meloxicam's role in insulin resistance is unexpected. In the present invention, the inventors demonstrate that meloxicam blocks or reduces the effect of compounds that induce or increase insulin resistance in in vitro models as well as in animal models of type 2 diabetes.

The present invention also encompasses the administration of meloxicam and niacin in further combination with other biological active ingredients, compounds, and non-drug therapies.

For example, meloxicam and niacin may further be combined with current anti-diabetic medicines such as glitazones, including, for example, rosiglitazone, pioglitazone, troglitazone, balaglitazone, and ragaglitazone to make them more effective. Anti-diabetic compounds that are also useful in combination with meloxicam (with or without niacin) include metformin, acarbose, miglitol, nateglinide, repaglinde, sitagliptin, and pramlinitide. Additionally, by administering the known anti-diabetic drugs at lower dosages and in combination with meloxicam and optionally niacin the safety profile of each component may be improved.

Additionally, the present invention also encompasses the administration of meloxicam and niacin further in combination with other drugs known for the treatment of dyslipidemia and other conditions associated with high cholesterol, low HDL, and/or high LDL. For example, meloxicam and niacin may be combined with current statin drugs, including, for example, atorvastatin, cerivastatin, fluvastatin, lovastatin, mevastatin, pitavastatin, pravastatin, rosuvastatin, simuvastatin, crestor, ezetimible, and combinations thereof.

As discussed herein, meloxicam can be combined with niacin to reduce insulin resistance and niacin-induced flushing.

Meloxicam in combination with the niacin can be administered to a subject by any conventional means and routes available for use in conjunction with pharmaceuticals, either as individual therapeutic compounds, as a combination of therapeutic compounds, or as independent multiple pharmaceutical compositions, or as a combination of multiple pharmaceutical compounds.

Thus, in the combination therapies, administration of meloxicam and niacin may take place sequentially in separate formulations, or may be accomplished by simultaneous administration in a single formulation or in a separate formulation. The combination formulation may be in the form of a single tablet or in the form of a bolus aqueous or non-aqueous isotonic sterile injection solution or suspension. The therapeutic compounds which make up the combination therapy may be administered in a combined dosage form, such as a tablet, or in separate dosage forms intended for substantially simultaneous oral administration.

As used herein, the terms "combination therapy," co-administration," "co-administering," "administration with," "administering," "combination," and/or "co-therapy," when referring to the use of meloxicam and niacin, are intended to embrace administration of each agent in a sequential manner in a regimen that will provide beneficial effects of the drug combination, and is intended, as well, to embrace co-administration of these agents in a substantially simultaneous manner.

Substantially simultaneous administration can be accomplished, for example, by administering to the subject the meloxicam in combination with the niacin, together in one therapeutic dosage form, such as in a single capsule, tablet, or injection, or in multiple separate therapeutic dosage forms, such as in separate capsules, tablets, or injections.

The therapeutic compounds of the combined therapy, whether administered simultaneously, substantially simultaneously, or sequentially, may involve a regimen calling for administration of one therapeutic compound by oral route and another therapeutic compound by another route. Thus, sequential or simultaneous administration of each therapeutic agent can be effected by any appropriate route including, but not limited to, oral routes, intravenous routes, intramuscular routes, subcutaneous routes, intraarticular routes, and direct absorption through mucous membrane tissues.

Sequential administration of such treatments encompasses both relatively short and relatively long periods between the administrations of each of the components of the present invention. With simultaneous administration, it may be preferred that the meloxicam be administered to the subject within the therapeutic response time of the administered niacin and vice versa.

As used herein, the terms "therapeutic response time" means the duration of time after administration that a compound has a therapeutic effect within a subject's body.

In certain aspects of the present invention, the meloxicam may be administered to a subject such that it reaches serum therapeutic levels before the administered niacin reaches serum levels that induce flushing. As a result, the earlier therapeutic level of the meloxicam will reduce the amount of flushing, which may result from the later therapeutic level of the niacin.

Thus, a regimen may call for sequential administration of the therapeutic compounds with spaced-apart ingestion of the separate, active agents. The time period between the multiple administration steps may range from, for example, a few minutes to several hours, depending upon the properties of each therapeutic compound such as potency, solubility, bioavailability, plasma half-life, and kinetic profile of the therapeutic compound, as well as depending upon the effect of food ingestion and the age and condition of the subject. Circadian variation of the target molecule concentration may also determine the optimal dose interval.

The administration of meloxicam in combination with niacin is an effective treatment for diabetes and diabetes-related conditions, such as insulin resistance and dyslipidemia, and in preferred embodiments, is superior to the use of either agent alone. Moreover, in preferred embodiments, the combination therapies of the present invention demonstrate a synergistic efficacy for treating and preventing diabetes and diabetes-related conditions such as insulin resistance that is greater than what would be expected from simply combining any of the individual monotherapies.

As used herein, the term synergistic encompasses the combination of meloxicam and niacin as a combined therapy having an efficacy for the prevention and treatment of insulin resistance that is greater than what would be expected merely from the sum of their individual effects. Optionally, however, the synergistic effects of the embodiments of the present invention's combination therapies can encompass other unexpected advantages for the treatment and prevention of insulin resistance. Such additional advantages include, but are not limited to, reducing the side effects of niacin-induced flushing and niacin-induced increase in insulin resistance, and thus, rendering those agents more tolerable to subjects in need of diabetes and diabetes-related conditions therapy.

In another aspect, the invention is a method of treating a subject in need of treatment and/or prevention of type 2 diabetes and/or related dyslipidemia by administering niacin in combination with meloxicam.

The subject invention involves the use of a therapeutically effective amount of meloxicam and niacin, thereby treating or preventing atherosclerosis and other conditions caused by dyslipidemia associated with type 2 diabetes. The subject in need of such treatment may also be in need of treatment and/or prevention of type 2 diabetes.

Accordingly, in certain aspects of the present invention, any component mentioned herein can be supplied in the form of a salt, a prodrug, an isomer, a tautomer, a racemic mixture, or in any other chemical form or combination that, under physiological conditions, still provides for any physiological function that the component may perform, including, but is not limited to, reduced niacin-induced flushing, reduced insulin resistance, reduced niacin-induced insulin resistance, increased HDL levels, and/or decreased LDL levels.

The present invention includes all possible diastereomers as well as their racemic and resolved, enantiomerically pure forms of any component described herein.

The compounds useful in the present invention can have no asymmetric carbon atoms, or, alternatively, the useful compounds can have one or more asymmetric carbon atoms. When the useful compounds have one or more asymmetric carbon atoms, they, therefore, include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis-isomers or trans-isomers across a double bond. All such isomers are contemplated among the compounds useful in the present invention. Also included in the methods, combinations and compositions of the present invention are the tautomeric forms of the described compounds.

The term "pharmaceutically acceptable" is used adjectivally herein to mean that the modified noun is appropriate for use in a pharmaceutical product.

The compounds of the present invention can also be supplied in the form of a pharmaceutically acceptable salt. The terms "pharmaceutically acceptable salt" means salts prepared from pharmaceutically acceptable inorganic and organic acids and bases.

Pharmaceutically acceptable inorganic bases include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary salts include aluminum, calcium, lithium, magnesium, potassium, sodium and zinc. Particularly preferred are the ammonium, calcium, magnesium, potassium, and sodium salts.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Illustrative pharmaceutically acceptable acid addition salts of the compounds of the present invention can be prepared from the following acids, including, without limitation formic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids.

In one embodiment, the meloxicam may be administered as an ethanolamine salt, including mono, di, and triethanolamine salts. See Han, H. *European Journal of Pharmaceuticals and Biopharmaceutics,* 65:99-103 (2007).

All of the above salts can be prepared by those skilled in the art by conventional means from the corresponding compound(s) of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference only with regards to the disclosures of pharmaceutically acceptable salts.

When the present combination therapy is supplied along with a pharmaceutically acceptable carrier, a pharmaceutical composition is formed.

A pharmaceutical composition of the present invention is directed to a composition suitable for the prevention or treatment of the disorders described herein. The pharmaceutical composition comprises meloxicam, niacin and at least one pharmaceutically acceptable carrier, or pharmaceutically acceptable excipient, which terms can be used interchangeably herein.

Pharmaceutically acceptable carriers and excipients are chosen such that side effects from the pharmaceutical compound(s) are minimized and the performance of the compound(s) is not canceled or inhibited to such an extent that treatment is ineffective.

The pharmaceutically acceptable carrier can also be selected on the basis of the desired route of administration of the compound(s). For example, in a preferred embodiment the carrier is suitable for oral administration. In some embodiments, the composition includes a carrier or additional agent that is suitable for promoting delivery of the compound(s) to the gastrointestinal or intestinal tract.

The carrier should be acceptable in the sense of being compatible with the other ingredients of the composition and not be deleterious to the recipient. The carrier can be a solid or a liquid, or both, and is preferably formulated with the compound(s) as a unit-dose composition, for example, a tablet, which can contain from 0.05% to 95% by weight of the active compound(s).

The pharmaceutical compositions of the invention can be prepared by any of the well-known techniques of pharmacy, for example, by admixing the components.

Whether the therapeutic compounds of the combined therapy are administered enterally or parenterally, separately or together, each therapeutic compound may be contained in a suitable pharmaceutical formulation of any of the pharmaceutically-acceptable excipients, diluents or other formulations components described herein.

Pharmaceutically acceptable carriers include, but are not limited to, physiological saline, Ringer's, phosphate solution or buffer, or buffered saline. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective. The term "pharmacologically effective amount" shall mean that amount of a drug or pharmaceutical agent that will elicit the biological or medical response of a tissue, system, animal or human that is being sought by a researcher or clinician. This amount can be a therapeutically effective amount.

The present pharmaceutical compositions may be administered enterally and/or parenterally. Parenteral administration includes subcutaneous, intramuscular, intradermal, intravenous, and other administrative methods known in the art. Enteral administration includes solution, tablets, enteric coated capsules, syrups, beverages, foods, and other nutritional supplements. When administered, the present pharmaceutical composition may be at or near body temperature.

In particular, the combination therapy of the present invention, or compositions in which they are included, can be administered orally, for example, as tablets, coated tablets, dragees, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example starch, gelatin, or acacia, and lubricating agents, for example magnesium stearate, stearic acid or talc. The tablets may be uncoated or they may be coated by known techniques.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, any of a variety of herbal extracts, milk, or olive oil.

Aqueous suspensions can be produced that contain the active materials in admixture with excipients suitable for the manufacture of aqueous suspensions. Such excipients are dispersing or wetting agents including naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the active ingredients in an omega-3 fatty acid, a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the present combination therapy may be formulated with sweetening agents, for example glycerol, sorbitol or sucrose. Such formulations may also contain a demulcent, a preservative, and flavoring and coloring agents.

The subject combination therapy and compositions in which it may be included can also be administered parenterally, either subcutaneously, or intravenously, or intramuscularly, or intrasternally, or by infusion techniques, in the form of sterile injectable aqueous or olagenous suspensions. Such suspensions may be formulated according to the known art using those suitable dispersing or wetting agents which have been mentioned above, or other acceptable agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, n-3 polyunsaturated fatty acids may find use in the preparation of injectables.

In most cases, the preferred route of administration is enteral (e.g., orally). Oral administration includes solution, tablets, sustained release capsules, enteric-coated capsules, and syrups. The pharmaceutical composition may be administered in dosage unit formulations containing conventional nontoxic pharmaceutically acceptable carriers, adjuvants, and vehicles as desired.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

The pharmaceutically acceptable carrier can also be selected on the basis of the desired route of administration of the compound(s). For example, in a preferred embodiment the carrier is suitable for oral administration.

The carrier should be acceptable in the sense of being compatible with the other ingredients of the composition and not be deleterious to the recipient. The carrier can be a solid or a liquid, or both, and is preferably formulated with the compound(s) as a unit-dose composition, for example, a tablet, which can contain from 0.05% to 95% by weight of the active compound(s).

Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, or olive oil.

Pharmaceutical compositions suitable for oral administration can be presented in discrete units each containing a predetermined amount of at least one therapeutic compound useful in the present invention; as a powder or granules; as a solution or a suspension in an aqueous or non-aqueous liquid; or as an oil-in-water or water-in-oil emulsion. As indicated, such compositions can be prepared by any suitable method of pharmacy, which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Syrups and elixirs containing the meloxicam and niacin may be formulated with sweetening agents, for example glycerol, sorbitol, or sucrose. Such formulations may also contain a demulcent, a preservative, and flavoring and coloring agents. Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Aqueous suspensions can be produced that contain the active materials in a mixture with excipients suitable for the manufacture of aqueous suspensions. Such excipients include dispersing or wetting agents, including naturally-occurring phosphatides, for example lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, or antioxidants such as ascorbic acid; one or more coloring agents; one or more flavoring agents; and/or one or more sweetening agents, such as sucrose or saccharin. Solutions and suspensions may be prepared from powders or granules having one or more pharmaceutically acceptable carriers or diluents, or a binder such as gelatin, together with one or more of a lubricant, preservative, surface active or dispersing agent.

Dispersible powders and granules suitable for preparation of an aqueous suspension by the addition of water provide the active ingredient in admixture with a dispersing or wetting agent, and one or more preservatives. Suitable dispersing or wetting agents are exemplified by those already mentioned above.

Oily suspensions may be formulated by suspending the active ingredients in an omega-3 fatty acid, a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol.

Also encompassed by the present invention is buccal or "sub-lingual" administration, which includes lozenges or a chewable gum comprising the compounds, set forth herein. The compounds can be deposited in a flavored base, usually sucrose, and acacia or tragacanth, and pastilles comprising the compounds in an inert base such as gelatin and glycerin or sucrose and acacia.

The subject method of prescribing meloxicam and/or niacin and compositions comprising the same can also be administered parenterally, for example, by either subcutaneously, or intravenously, or intramuscularly, or intrasternally, or by infusion techniques, in the form of sterile injectable aqueous or olageneous suspensions. Such suspensions may be formulated according to the known art using those suitable dispersing or wetting agents, which have been mentioned above, or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Pharmaceutical compositions suitable for parenteral administration can conveniently comprise sterile aqueous preparations of a compound of the present invention. These preparations are preferably administered intravenously, although administration can also be effected by means of subcutaneous, intramuscular, or intradermal injection or by infusion. Such preparations can conveniently be prepared by admixing the compound with water and rendering the resulting solution sterile and isotonic with the blood. Injectable compositions according to the invention will generally contain from 0.1 to 10% w/w of a compound disclosed herein.

Injectable preparations, for example, sterile injectable aqueous or oleaginous suspensions may be formulated according to the known art using suitable dispersing or setting agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The active ingredients may also be administered by injection as a composition wherein, for example, saline, dextrose, or water may be used as a suitable carrier. A suitable daily dose of each active therapeutic compound is one that achieves the same blood serum level as produced by oral administration as described above.

Pharmaceutical compositions suitable for topical application to the skin preferably take the form of an ointments, creams, lotions, pastes, gels, sprays, powders, jellies, collyriums, solutions or suspensions, aerosols, or oils. Carriers, which can be used, include petroleum jelly (e.g., Vaseline®), lanolin, polyethylene glycols, alcohols, and combinations of two or more thereof. The active compound or compounds are generally present at a concentration of from 0.1 to 50% w/w of the composition, for example, from 0.5 to 2%.

The present invention may also include safe and effective amounts of isotonicity agents, e.g., salts, such as sodium chloride, and more preferably non-electrolyte isotonicity agents such as sorbitol, and mannitol.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically, such co-solvents are employed at a level of from 0.01% to 2% by weight.

Pharmaceutically acceptable excipients and carriers encompass all the foregoing and the like. The above considerations concerning effective formulations and administration procedures are well known in the art and are described in standard textbooks. See e.g. Gennaro, A. R., *Remington: The Science and Practice of Pharmacy*, 20$^{th}$ Edition, (Lippincott, Williams and Wilkins), 2000; Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., *Handbook of Pharmaceutical Excipients* (3$^{rd}$ Ed.), American Pharmaceutical Association, Washington, 1999.

In the present method, a subject in need of treatment and/or prevention of type 2 diabetes and/or related conditions such as dyslipidemia may be treated with an amount of the present combination therapy, where the amount of the individual components provides a dosage or amount that is sufficient to constitute a treatment or prevention effective amount.

As used herein, an "effective amount" means the dose or amount of the present combination therapy to be administered to a subject and the frequency of administration to the subject which is readily determined by one of ordinary skill in the art, by the use of known techniques and by observing results obtained under analogous circumstances and has some therapeutic action. The dose or effective amount to be administered to a subject and the frequency of administration to the subject can be readily determined by one of ordinary skill in the art by the use of known techniques and by observing results obtained under analogous circumstances.

The phrase "therapeutically-effective" and "effective for the treatment, prevention, or inhibition," mean the amount of each agent for use in the therapy which will achieve the goal of decreased insulin resistance decreased LDL levels, and/or increased HDL levels, while avoiding adverse side effects typically associated with niacin use.

The amount of compound in combination that is required to achieve the desired biological effect will, of course, depend on a number of factors such as the specific compound chosen, the use for which it is intended, the mode of administration, and the host to be treated and the clinical condition of the recipient.

For purposes of the present invention, it is preferred that the amount of meloxicam and the amount of niacin together comprise an effective amount of the combination of the two treatment agents. Still further preferred is that the amount of the co-therapy with the meloxicam and niacin comprises a therapeutically effective amount of the co-therapy.

Thus, in a preferred embodiment, the present invention provides a method of preventing or treating diabetes and/or related dyslipidemia in a subject comprising administering an amount of meloxicam and an amount of niacin wherein the amount of the meloxicam and the amount of the niacin together comprises a therapeutically effective amount.

A diabetes and/or related dyslipidemia symptom is considered ameliorated or improved if any benefit is achieved, no matter how slight. Likewise, a diabetes and/or related dyslipidemia symptom is considered ameliorated or improved if any benefit is achieved, no matter how slight.

As used herein, the terms "prophylactically effective" refer to an amount of meloxicam in combination with niacin that causes a decrease in the frequency of incidence of diabetes and/or related dyslipidemia. The term "prophylactic" refers to the prevention of diabetes and/or related dyslipidemia, whereas the term therapeutic refers to the effective treatment of an existing diabetes and/or related dyslipidemia.

It will be appreciated that the amount of the meloxicam and the niacin required for use in the treatment or prevention of diabetes and/or related dyslipidemia will vary within wide limits and will be adjusted to the individual requirements in each particular case. In general, for administration to adults, an appropriate daily dosage is described herein, although the limits that are identified as being preferred may be exceeded if expedient.

The dosage of niacin for the present method optionally ranges from about 1 to about 100 mg/kg/day and preferably from about 7 to about 45 mg/kg/day and the dosage for meloxicam for the present method optionally ranges from about 0.01 to about 1 mg/kg/day and preferably from about 0.1 to about 0.22 mg/kg/day.

In general, for administration to adults, an appropriate daily dosage is described herein, although the limits that are identified as being preferred may be exceeded if expedient. The daily dosage can be administered as a single dosage or in divided dosages. It is understood, however, that specific dose levels of the therapeutic agents or therapeutic approaches of the present invention for any particular subject depends upon a variety of factors including the activity of the specific compound employed, the age, body weight, general health, sex, and diet of the subject, the time of administration, the rate of excretion, the drug combination, the severity of the particular disease being treated and form of administration, and the individual responsiveness of the subject to be treated, and other relevant circumstances.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of diabetes and/or related dyslipidemia in accordance with the present invention. In terms of treatment protocols, it should be appreciated that the dosage to be administered will depend on several factors, including the particular agent that is administered, the route administered, the condition of the particular patient, etc.

Dosages for the combination therapy provided herein may be determined and adjusted based on the efficacy demonstrated in reducing or preventing the symptoms of diabetes and/or related dyslipidemia. In addition, one of ordinary skill in the art will know how to measure and quantify the presence or absence of diabetes, insulin resistance and/or related dyslipidemia symptoms.

Preferred dosages for the combination therapy are those that are effective to increase HDL, decrease LDL, decrease insulin resistance, and/or decrease prostaglandin production. In especially preferred embodiments, the dosage should be in a concentration effective to decrease insulin resistance such that treatment and/or prevention of type 2 diabetes is effected. In yet another embodiment an effective dosage is an amount that is affective to increase HDL levels in the subject. In some embodiments, an effective dosage is an amount that is affective to decrease LDL levels in the subject. In another embodiment, an effective dosage is an amount that is effective to reduce or block rapid prostaglandin production upon administration of niacin to the subject.

For purposes of calculation of dosage amounts, the weight of a normal adult human will be assumed to be 70 kg.

For the purposes of calculating and expressing a dosage rate, all dosages that are expressed herein are calculated on an average amount-per-day basis irrespective of the dosage rate. For example, one 20 mg dosage of meloxicam taken once every two days would be expressed as a dosage rate of 10 mg/day. Similarly, the dosage rate of an ingredient where 50 mg is taken twice per day would be expressed as a dosage rate of 100 mg/day.

The amount of the meloxicam that may be combined with the niacin and carrier materials will vary depending upon the host treated and the particular mode of administration. For example, a formulation intended for the oral administration of humans may range from about 0.5 mg to about 100 mg of meloxicam compounded optionally with an appropriate and convenient amount of carrier material, which may vary from about 5 to about 95 percent of the total composition. Dosage unit forms for the meloxicam will generally contain between from about 0.5 mg to about 25 mg of an active ingredient, typically 0.5 mg, 1 mg, 2.5 mg, 5 mg, 7.5 mg, 10 mg, 15 mg, or 25 mg.

In the subject invention, the niacin can be used in combination with the meloxicam in any amount that is an effective amount. The amount of the niacin that may be combined with the carrier materials to produce a single dosage form will vary depending upon the host treated and the particular mode of administration. For example, a formulation intended for the oral administration of humans may contain from 100 mg to 3 g per day of active agent compounded optionally with an appropriate and convenient amount of carrier material, which may vary from about 5 to about 95 percent of the total composition. Dosage unit forms for the niacin will generally contain between from about 100 mg to about 3000 mg of an active ingredient, typically 100 mg, 200 mg, 300 mg, 400 mg, 500 mg, 750 mg, 1000 mg, 1500 mg, 2000 mg, 2500 mg, or 3000 mg.

The combination of niacin and meloxicam may be administered on a regimen of once or several times per day, for example 1 to 4 times per day, preferably once per day, and preferably at night.

The frequency of dose will depend upon the half-life of the meloxicam and niacin compounds. In certain embodiments, the daily dosage can be administered as a single dosage or in divided dosages.

Those skilled in the art will also appreciate that dosages may also be determined with guidance from Goodman & Gilman's *The Pharmacological Basis of Therapeutics*, Ninth Edition (1996), Appendix II, pp. 1707-1711.

Accordingly, therefore, in an embodiment of the compositions or formulations of the present invention, the ratio of meloxicam-to-niacin by weight may be from about 0.000017:1 to about 0.25:1, or from about 0.0001:1 to about 0.1:1 or from about 0.005:1 to about 0.03:1.

The following examples describe exemplary embodiments of the present invention. Other embodiments with the scope of the claims herein will be apparent to one skilled in the art from consideration of the specification or practice of the inventions as disclosed herein. It is intended that the specification, together with the examples, be considered to be exemplary only, with the scope and the spirit of the invention being indicated by the claims which follow the examples. In the examples, all percentages are given on a weight basis unless otherwise indicated.

EXAMPLE 1

This example illustrates that meloxicam decreases niacin induced- or TNFα induced-IRS phosphorylation in an adipocyte cell model. TNFα or niacin induced the phosphorylation of insulin receptor substrate (IRS-1), a measure of their ability to interfere in insulin signaling and cause insulin resistance. The addition of meloxicam was shown to block IRS phosphorylation induced by these agents, indicating its ability to improve insulin resistance.

Murine 3T3L1 cells (ATCC CL-173) were cultured in DMEM (ATCC 30-2002) supplemented with 10% Bovine Calf Serum (BCS) (Colorado Serum Co. CS1334). Differentiation was induced by exposing confluent cells to insulin (1 µM), isobutylmethylxanthine (0.5 mM) and dexamethasone (0.25 µM) (all from Sigma) for 2 days and then to insulin (1 µM) alone for an additional 2 days. The medium was changed every 2 days until completer differentiation was achieved. Cells were maintained in DMEM containing 10% BCS.

Prior to treatments, adipocytes were incubated overnight in low serum medium (DMEM containing 1% BCS). Cells were incubated with compounds/low serum medium for 2 hours prior to niacin/TNFα exposure. Niacin for cell exposure was prepared as an aqueous 2 M stock solution, which was then diluted further in low serum medium. Cells were exposed to varying concentrations of niacin (0.1-3 mM) for varying times 30 mins-1 hr). Cells were exposed to TNFα (20 ng/mL) for 30 minutes.

Following treatments, cells were harvested in cell lysis buffer (Pierce) containing protease inhibitors. Protein concentrations were determined using the micro BCA assay (Pierce).

Cell lysates were resuspended in SDS-loading buffer (Invitrogen) and separated in pre-cast loaded on 4-20% gradient NuPAGE gels (Invitrogen). Proteins were transferred on to polyvinylidene difluoride (PVDF) membranes and blocked overnight in blocking solution (KPL). Membranes were probed with anti-phospho IRS1 (S307) antibodies (UpState) according to manufacturer's protocol. Detection was performed with ECLPlus chemiluminescent substrate system (Amersham Biosciences). Bands were quantitated using TotalLab™ quantitation software. Membranes were stripped using RestorePlus stripping buffer (Pierce) and reprobed with anti-IRS1 antibodies that react with total IRS1 protein. Band intensity values obtained for the anti-phospho IRS1 Western blot were normalized to values obtained for the IRS1 Western blot. Insulin resistance (IR) in 3T3L1 was determined by measuring Ser307 phosphorylation of IRS-1.

FIG. 1 illustrates the results of Example 1, which shows that in the presence of niacin alone IRS-1 phosphorylation is significantly increased indicating impaired insulin signaling. Compared to untreated, niacin increased IRS-1 phosphorylation and this was inhibited by meloxicam. Also, compared to untreated, TNFα increased IRS1 phosphorylation and this was inhibited by meloxicam. Thus, when meloxicam is combined with niacin, IRS-1 phosphorylation was significantly reduced.

EXAMPLE 2

This example illustrates the niacin and meloxicam combination effect on insulin resistance, and lipids in a db/db−/− diabetic mouse model. An increase in circulating levels of insulin is one of the symptoms of insulin resistance and type 2 diabetes. In db/db mice, a model of type 2 diabetes, there is an increase in plasma insulin levels. Treatment with a low dose of meloxicam (2 mg/kg/day) for two weeks reduced insulin levels, suggesting its ability to treat hyperinsulinemia.

To evaluate the niacin and meloxicam effect on plasma glucose, insulin resistant and lipids in db/db−/− diabetic mouse model were measured. The animals were 40 Female db/db diabetic mice, 4 weeks old on a diet of normal rodent chow. The tests were conducted on five groups, with 7-8 mice per group.

Group 1: Control CMC-tween, oral pipetting, 7 mice. Once a day for 28 days, 60 µl/mouse.

Group 2: Niacin 2.5 g/kg (roughly), in drinking water for 28 days, 7 mice (10 mg/mL in water).

Group 3: Meloxicam 2 mg/kg, oral pipetting, 7 mice. Once a day for 28 days, 30 ul/mouse. (2 mg/mL in water)

Group 4: Niacin and meloxicam, 8 mice. Once a day for 28 days [niacin: 2.5 g/kg in drinking water (10 mg/ml in water), meloxicam: 30 µL/mouse. (2 mg/mL in water)].

Group 5: Pioglitazone 30 mg/kg/day, oral pipetting, 7 mice. Once a day for 28 days, 60 µL/mouse. (15 mg/mL in Vehicle)

Body weight was measured in all groups once a week. Food consumption was monitored once a week. All animals were fasted for 4 hours and plasma glucose levels were measured by OneTouch™ Ultra blood glucose meter. 35 animals were divided to 5 groups with 7 mice per group base on plasma glucose level. (Plasma glucose >120 mg/dL as a cut off for animal selection). 200 µL blood samples were collected from retro-orbital vein for plasma insulin level and lipids profile at baseline.

Treatment started for all groups and lasted for 28 days. 4 hours fast blood samples were collected for plasma insulin level and lipids profile at 2 weeks and 4 weeks post dose. The Oral Glucose Tolerance Test ("OGTT") was conducted at day 16 and day 30 post dose.

OGTT Procedure:

All animals were fasted for 4 hours, plasma glucose level were measured by OneTouch™ Ultra blood glucose meter. Dextrose solutions (200 mg/mL in water) at 2 g/kg dose were administrated to all animals by oral gavage. Plasma glucose levels were measured by OneTouch™ Ultra blood glucose meter at 15 minutes, 50 minutes, 80 minutes, 120 minutes and 155 minutes post Glucose dose.

Figure 2:
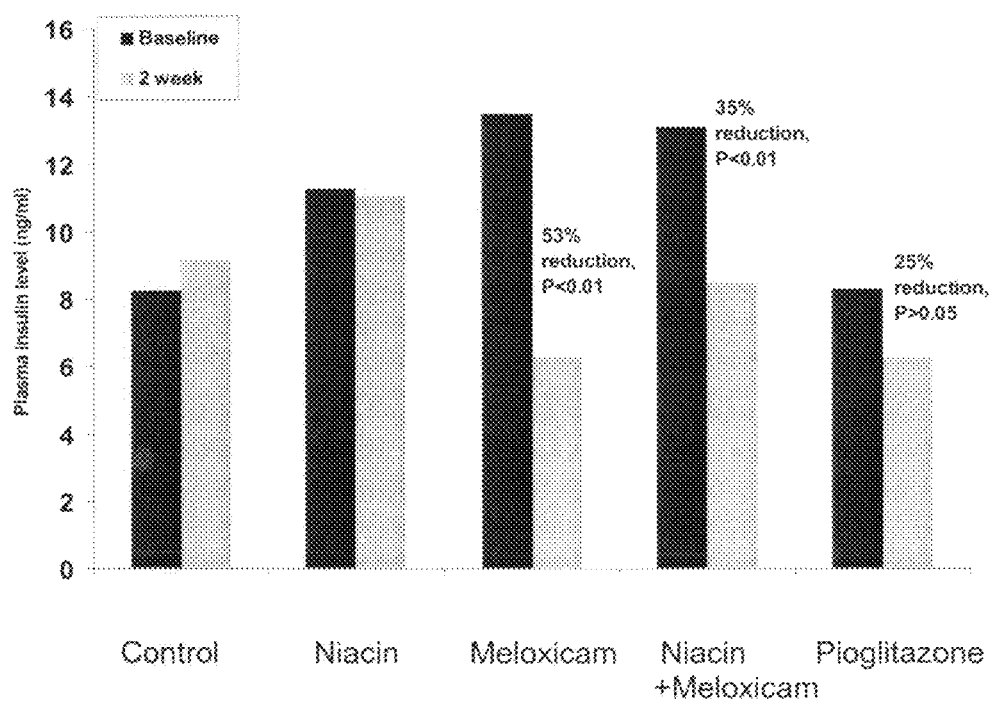
FIG. 2 is a chart demonstrating the effect of meloxicam on plasma insulin levels in db/db mice, a mouse model of insulin resistance and diabetes.

The results of Example 2 are shown in FIG. 2, which indicates that meloxicam alone or in combination with niacin significantly reduced plasma insulin, an indicator of a reduction in an insulin resistant state. The degree of effect was similar to that seen with a known insulin sensitizer, pioglitazone.

Figure 3:
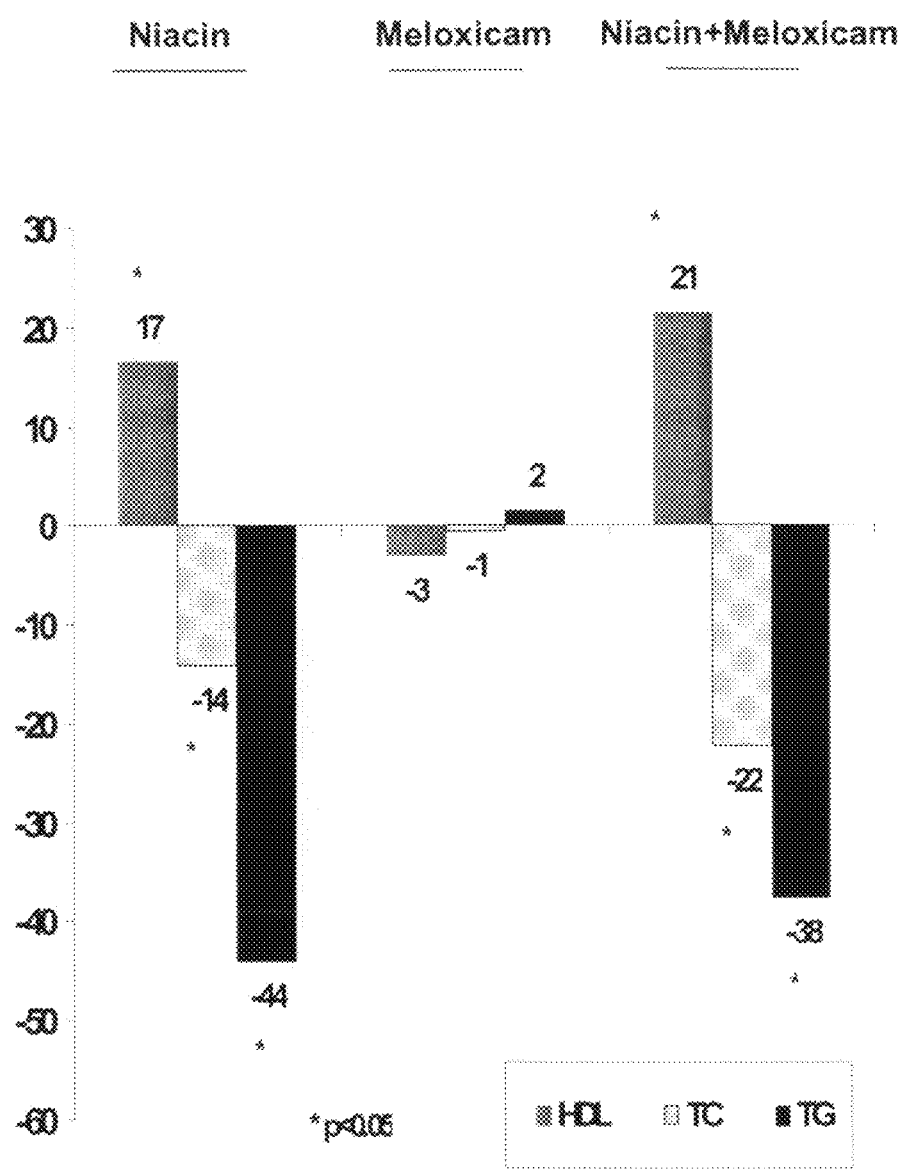
FIG. 3 is a chart demonstrating the effect of niacin and combination on insulin resistance, and lipids in a db/db-/- diabetic mouse model.

Addition of meloxicam did not affect niacin's ability to increase HDL or decrease triglycerides in this diabetic dyslipidemia model. The results are shown in FIG. 3

EXAMPLE 3

This example illustrates an in vitro and in vivo assay for niacin-induced flushing.

Anti-inflammatory effects of meloxicam were examined in an in vitro cell based system and in mouse. Addition of niacin induced the formation of PGD2, an inflammatory prostaglandin and inducer of flushing. The addition of meloxicam reduces the formation of PGD2, indicative of its anti-flushing activity.

The human monocyte cell line THP-1 was differentiated into functional macrophages by exposure to the protein kinase C activator PMA (phorbol ester). Prostaglandin D2 (PGD2) secretion was measured in this cell line in response to niacin and combination treatments.

THP-1 cells were plated in 24 well plates in growth medium (PRMI1640 containing 10% serum and 2-beta mercaptoethanol (BME)) containing 200 nM PMA. Plates were incubated at 37° C. for 72 hours. Media was then replaced with growth media (with no PMA) for 2 days prior to treatments.

Niacin for cell exposure was prepared as an aqueous 2 M stock solution, which was then diluted further in treatment medium (RPMI 1640). Cells were incubated in diluted treatment media for 30 minutes prior to niacin exposure. Cells were then exposed to different concentrations of niacin (0.1 mM and 3 mM) for varying times (5-60 minutes).

PGD2 was measured using a commercially available competitive enzyme assay kit (Cayman Chemical, Ann Arbor, Mich.). Since PGD2 is unstable, all samples underwent a chemical conversion to a more stable PGD2 methoxime (PGD2-MOX) form prior to assay. This derivatization was done according to the manufacturer's instructions. Samples were incubated overnight at 4° C. in 96 well plates that were pre-coated with mouse monoclonal anti-rabbit IgG, in the presence of rabbit PGD2-MOX (either free or tracer linked) and rabbit antibody binds to the pre-coated plates. The plates are then washed and a solution containing acetylcholine esterase reagent is added to the wells. Following incubation at room temperature, absorbance was read at 412 nm.

Figure 4:
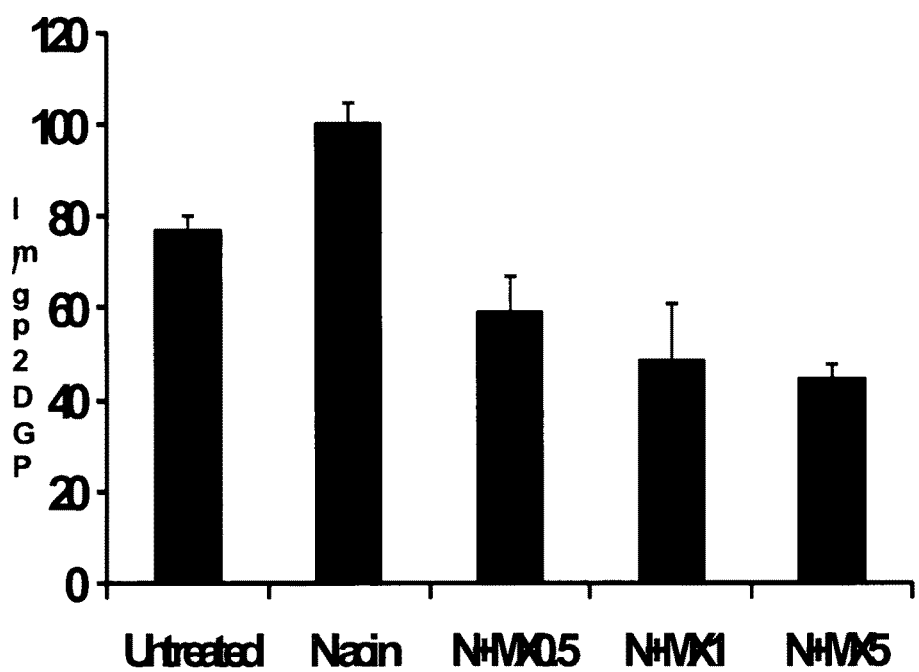
FIG. 4 is a chart demonstrating the effect of meloxicam on niacin-induced prostaglandin PGD2 production (an indicator of flushing) in cell cultures.

The results are expressed as pg of PGD2-MOX derived from a standard curve. The results of Example 3 are shown in FIG. 4, which indicates that compared to controls, niacin increased PGD2 levels in culture medium, and that the increase in PGD2 levels were inhibited in the presence of meloxicam.

Figure 5:
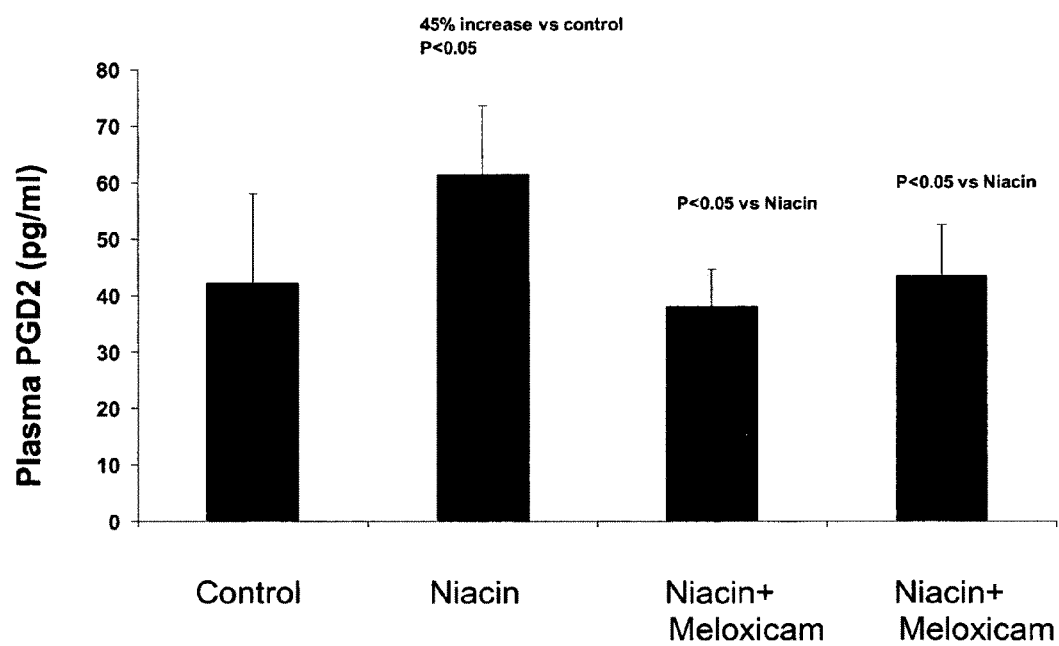
FIG. 5 is a chart demonstrating the effect of meloxicam on PGD2 levels in an animal model.

The effect of meloxicam on PGD2 levels in an animal model is shown in FIG. 5.

In view of the above, it will be seen that the several advantages of the invention are achieved and other advantageous results obtained.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. A method of treating dyslipidemia in a subject having type 2 diabetes, the method comprising administering to the subject niacin in combination with meloxicam, wherein the meloxicam is administered in an amount that reduces niacin-induced insulin resistance in the subject.

2. The method according to claim 1, wherein the meloxicam is administered in an amount that reduces niacin-induced flushing and niacin-induced insulin resistance in the subject.

3. The method according to claim 1, wherein the niacin is administered in an amount that has at least one effect that is selected from the group consisting of increasing the HDL level, decreasing the LDL level, and reducing the triglyceride level, all in the subject's blood stream.

4. The method according to claim 1, wherein the meloxicam is administered to the subject before the administration of the niacin.

5. The method according to claim 1, wherein the meloxicam is administered to the subject simultaneously with the administration of the niacin.

6. The method according to claim 1, wherein the meloxicam is administered in an amount that is sufficient to block and/or reduce rapid production of prostaglandin resulting from the administration of niacin.

7. The method according to claim 1, wherein the niacin is administered in an amount sufficient to increase HDL and decrease LDL in the subject and the meloxicam is administered in an amount sufficient to reduce insulin resistance in the subject while blocking and/or reducing prostaglandin production resulting from the administration of niacin.

8. The method according to claim 1, further comprising administering to the subject an anti-dyslipidemic drug selected from the group consisting of atorvastatin, cerivastatin, fluvastatin, lovastatin, mevastatin, pitavastatin, pravastatin, rosuvastatin, simuvastatin, crestor, ezetimible, and combinations thereof.

9. A method of treating dyslipidemia in a subject having type 2 diabetes comprising administering to the subject niacin in combination with meloxicam and an anti-diabetic drug selected from the group consisting of rosiglitazone, pioglitazone, troglitazone, acarbose, migiltol, nateglinide, repaglinide, sitagliptin, pramlintide, metformin, and combinations thereof.

10. A method of treating dyslipidemia in a subject having type 2 diabetes, the method comprising administering to the subject niacin in combination with meloxicam, wherein the meloxicam is administered in an amount of from about 0.01 to about 1 mg/kg/day and the niacin is administered in an amount of from 1 to about 100 mg/kg/day.

11. A method of treating dyslipidemia in a subject having type 2 diabetes, the method comprising administering to the subject niacin in combination with meloxicam, wherein the meloxicam is administered in an amount of from about 0.1 to about 0.22 mg/kg/day and the niacin is administered in an amount of from about 7 to about 45 mg/kg/day.

* * * * *